US009346931B2

(12) United States Patent
Odriozola et al.

(10) Patent No.: US 9,346,931 B2
(45) Date of Patent: May 24, 2016

(54) SELF-HEALING MATERIAL AND METHOD FOR THE PREPARATION THEREOF

(71) Applicant: FUNDACIÓN CIDETEC, Donostia (ES)

(72) Inventors: Ibón Odriozola, Donostia (ES); Pablo Casuso, Donostia (ES); Natividad Díaz, Donostia (ES); Iraida Loinaz, Donostia (ES); Germán Cabañero, Donostia (ES); Hans-jürgen Grande, Donostia (ES)

(73) Assignee: Fundación Cidetec, Donostia (ES)

( * ) Notice: Subject to any disclaimer, the term of this patent is extended or adjusted under 35 U.S.C. 154(b) by 5 days.

(21) Appl. No.: 14/360,598

(22) PCT Filed: Nov. 27, 2012

(86) PCT No.: PCT/EP2012/073693
§ 371 (c)(1),
(2) Date: May 23, 2014

(87) PCT Pub. No.: WO2013/079469
PCT Pub. Date: Jun. 6, 2013

(65) Prior Publication Data
US 2014/0329267 A1 Nov. 6, 2014

Related U.S. Application Data

(60) Provisional application No. 61/583,019, filed on Jan. 4, 2012.

(30) Foreign Application Priority Data

Nov. 28, 2011 (EP) ..................... 11382365

(51) Int. Cl.
*C08K 3/08* (2006.01)
*C08G 65/326* (2006.01)
*C08G 65/334* (2006.01)
*C08L 71/02* (2006.01)
*C07C 323/12* (2006.01)
*C07K 14/78* (2006.01)
*C08B 37/08* (2006.01)
*C08F 222/38* (2006.01)
*C08G 18/38* (2006.01)
*C08G 18/76* (2006.01)
*C08G 77/28* (2006.01)
*C09D 133/26* (2006.01)
*C09D 175/08* (2006.01)
*C09D 183/08* (2006.01)

(52) U.S. Cl.
CPC ............... *C08K 3/08* (2013.01); *C07C 323/12* (2013.01); *C07K 14/78* (2013.01); *C08B 37/0072* (2013.01); *C08F 222/38* (2013.01); *C08G 18/3863* (2013.01); *C08G 18/7657* (2013.01); *C08G 65/326* (2013.01); *C08G 65/334* (2013.01); *C08G 77/28* (2013.01); *C08L 71/02* (2013.01); *C09D 133/26* (2013.01); *C09D 175/08* (2013.01); *C09D 183/08* (2013.01); *C08K 2003/085* (2013.01); *C08K 2003/0806* (2013.01); *C08K 2003/0831* (2013.01); *C08L 2203/02* (2013.01)

(58) Field of Classification Search
CPC .... C08B 37/072; C08G 77/28; C08G 65/334; C08K 3/08; C08K 2003/0806; C08K 2003/0831; C08K 2003/085
See application file for complete search history.

(56) References Cited

U.S. PATENT DOCUMENTS 7,354,600 B1    4/2008  Bernkop-Schnürch

FOREIGN PATENT DOCUMENTS

WO    WO 2010/087912    8/2010
WO    WO 2010/128007    11/2010

OTHER PUBLICATIONS

Toh, H.S., et al.; Science China Chemistry, 2014, p. 1199-1210.*
International Search Report for PCT/EP2012/073693, mailed Jan. 31, 2013, 11 pgs.
Beck et al., "Multistimuli, Multiresponsive Metallo-Supramolecular polymers" J. of Am. Chem. Soc. vol. 125, pp. 13922-13923 (2003).
Bell et al., "Self-assembling peptides as injectable lubricants for osteoarthritis", J. of Biomed. Mat. Res. Part A, pp. 236-246 (2006).
Bernkop-Schnürch "Thiomers: A new generation of mucoadhesive polymers", Advanced Drug Delivery Reviews 57, pp. 1569-1582 (2005).
Bokern et al., "Synthesis of New Thermoplastic Elastomers by Silver Nanoparticles as Cross-Linker", Macromolecules vol. 44, pp. 5036-5042 (2011).
Bulaj et al., "Ionization-Reactivity Relationships for Cysteine Thiols in Polypeptides", Biochemistry 17, pp. 8965-8972 (1998).
Canadell et al., "Self-Healing materials based on disulfide links", Macromolecules vol. 44, pp. 2536-2541 (2011).
Chew "Curing characteristics and elastic recovery of sealants", Building and Environment 36, pp. 925-929 (2001).
Cho et al., "Self-Healing Polymer Coatings", Adv. Mater. 21, pp. 645-649 (2009).

(Continued)

*Primary Examiner* — Robert Jones, Jr.
(74) *Attorney, Agent, or Firm* — Squire Patton Boggs (US) LLP

(57) ABSTRACT

It is provided a self-healing polymer network comprising transition metal thiolates, particularly thiolates of a transition metal that is able to self-assemble by metallophilic attractions, and more particularly Au(I), Ag(I), Cu(I) thiolates, or a mixture thereof, and, optionally, disulfide bonds, thiol and other thiolate groups. It is also provided several processes for the preparation of the self-healing polymer networks of the invention, as well as uses thereof.

20 Claims, 5 Drawing Sheets

(56) References Cited

OTHER PUBLICATIONS

Chung et al., "Evaluation of micro-replication technology using silicone rubber molds and its applications", Int. J. of Machine Tools & Manufacture 43, pp. 1337-1345 (2003).

Drury et al., "Hydrogels for tissue engineering: scaffold design variables and applications", Biomaterials 24, pp. 4337-4351 (2003).

Gimeno et al., "Three-and Four-Coordinate Gold(I) Complexes", Chem. Reviews vol. 97, No. 3, pp. 512-522 (1997).

Hill et al., "Gold-197 Mössbauer Studies of Some Gold(I) Thiolates and Their Phosphine Complexes Including Certain Antiarthritic Gold Drugs", Inorg. Chem, 22, pp. 2936-2942 (1983).

Hoare et al., "Hydrogels in drug delivery: Progress and challenges", Polymer 49 pp. 1993-2007 (2008).

Hoffman "Hydrogels for biomedical applications", Advance Drug Delivery Reviews 43, pp. 3-12 (2002).

Isab et al., "Synthesis and characterization of thiolate-Ag(I) complexes by solid-state and solution NMR and their antimicrobial activity", Spectrochimica Acta Part A 66, pp. 364-370 (2007).

Jin et al., "Fracture and fatigue response of a self-healing epoxy adhesive", Polymer 52, pp. 1628-1634 (2011).

Keshavaraj et al., "Effects of moisture on structural silicone rubber sealants used in window glazing applications", Construction and Building Materials vol. 8, No. 4, pp. 227-232 (1994).

Shaw III., "Gold-Based Therapeutic Agents", Chem. Rev. 99, pp. 2589-2600 (1999).

Song et al., "A self-repairing polymer waveguide sensor", Smart Mater. Struct. 20, 12 pgs. (2011).

Yun et al., "A performance evaluation method of preformed joint sealant: Slip-down failure", Construction and Building Materials vol. 25, pp. 1677-1684 (2011).

Yu-Shiun Chen "Assessment of the in Vivo Toxicity of Gold Nanoparticles", Nanoscale Res Lett 4, pp. 858-864 (2009).

\* cited by examiner

SELF-HEALING MATERIAL AND METHOD FOR THE PREPARATION THEREOF

This application claims the benefit of European Patent Application No. 11382365.2, filed on Nov. 28, 2011, and U.S. Provisional Patent Application Ser. No. 61/583,019 filed on Apr. 1, 2012.

FIELD OF THE INVENTION

The present invention relates to the field of polymer chemistry, more particularly to self-healing materials. In particular, the invention relates to a self-healing polymer network and to processes for its preparation. Such polymer network can be a gel (an organogel or a hydrogel) or an elastomeric material. The invention also relates to the use of the new self-healing polymer networks.

BACKGROUND ART

Self-healing materials are of interest due to their many potential applications, providing a unique promising platform for environmental and physiological applications. A self-healing polymer must possess the ability to form multiple bonding interactions in and around the damaged area, creating connections between the components that make up its structure. To date, this challenge has been treated with four different strategies: (a) encapsulation of reactive monomers that are released after a fracture, (b) the formation of new irreversibly covalent bonds in the damaged area, (c) supramolecular self-assembly, and (d) the formation of reversible covalent bonds.

Encapsulation of monomers has been used successfully for some applications, but the irreversible nature of the healing mechanism is a limitation, as the repair can occur only once in the same place. The same applies for irreversible covalent bonds that are induced in the damaged area. A particularly useful approach to generate self-healable polymers has been the introduction of reversible bonds or cross-links into the polymer network. Thus, chemical cross-links which are broken when the material fractures can be reconnected again, restoring the integrity of the material. However, most reversible covalent systems developed to date require the use of heat, light or other energy for the reaction to take place, which greatly limits its practical application.

WO2010128007A1 discloses a self-healing polymer comprising disulfide bonds, wherein self-healing is achieved by interchange reaction via the disulfide-bonds. Nevertheless, healing is only achieved after heating at temperatures higher to 60° C., and mechanical properties are fully restored only at the mentioned temperature after one hour.

WO2010087912A1 discloses a composite comprising the reaction product between a macromolecule comprising at least one thiol and a gold nanoparticle. The thiolated macromolecules cross-link with the gold nanoparticles to form a hydrogel which is useful for cell anchoring. Nevertheless the process takes place with a slow cross-linking speed (the hydrogel is obtained after a minimum of 24 hours from mixing the components) and reversible cross-linking can only effectively take place among freshly prepared hydrogel structural elements. Additionally, toxicity of Au nanoparticles is still a controversial issue in the scientific literature (Y-S. Chen, et al. "Assessment of the In Vivo Toxicity of Gold Nanoparticles", Nanoscale Res. Lett., 2009, vol. 4, pp. 858-864).

While various self-healing materials have heretofore been disclosed in the literature, there continues being a need of a polymer system with self-healing properties providing superior benefits, especially in the biomedical field.

SUMMARY OF THE INVENTION

Inventors have found a self-healing polymer network having improved properties, the polymer network comprising thiolate groups, and optionally disulfide bonds, such thiolate groups or part of them being in the form of transition metal thiolates (—S-M, wherein M is a transition metal cation), preferably of thiolates of a transition metal that is able to self-assemble by metallophilic attractions, more preferably thiolates of Au(I), Ag(I) or Cu(I). The system is especially useful for the preparation of self-healing gels (organogels or hydrogels) and elastomeric materials.

Advantageously, the introduction of —S-M groups wherein M is a transition metal cation that is able to self-assemble by metallophilic attractions to form aggregates, such as Pd(II), Cd(II), Pt(II), Hg(II), Pb(II), Tl(I), Ir(I), Au(I), Ag(I) and Cu(I), provide additional cross-links into the polymer network resulting in a material endowed with a surprisingly high self-healing ability. Preferably, M is a monovalent transition metal cation selected from Au(I), Ag(I) and Cu(I). According to this particular embodiment, surprisingly, the self-healing polymer network is obtained at room temperature and in a few seconds or minutes in situ.

Thus, a first aspect of the invention is the provision of a self-healing polymer network comprising at least one polymer chain functionalized with at least two sulfur atoms in the form of thiol, thiolate, or forming part of a disulfide, or a mixture thereof, wherein from 0.1-100% of the sulfur atoms are in the form of at least one transition metal thiolate (—S-M), and from 99.9-0% of said sulfur atoms are in the form of thiol, a thiolate other than a transition metal thiolate, or forming part of a disulfide until completing 100% of the sulfur atoms in the form of disulfide, thiol, or thiolate, provided that if there are not cross-links in form of disulfide, then the at least one transition metal (M) forming the transition metal thiolate is a transition metal that is able to self-assemble by metallophilic attractions.

In case of fracture, the self-healing process of the polymer network of the invention takes place in a reduced period of time and without the need of any external stimulus, such as heat or light. So, when the gel (an organogel, or a hydrogel) or elastomeric material is cut into two pieces it restores again, in some cases even in a question of seconds, by just putting the pieces in contact together. Beside this, the self-healing ability of the material of the invention does not depend on the number of breaking-repairing cycles it is submitted to, but the process can be repeated many times without observing any decrease in the self-healing power. The obtained polymer networks maintain their self-healing ability for more than one month.

In a second aspect the invention relates to a process for the preparation of the self-healing polymer network of the invention, the process comprising reacting: a) at least one polymer functionalized with at least two thiols, with b) at least one transition metal salt or complex, in the presence of a base, wherein: if the polymer in a) is functionalized with only two thiols, then the transition metal forming the transition metal salt or complex is a transition metal that is able to self-assemble by metallophilic attractions; or if the polymer in a) is functionalized with more than two thiols then either the transition metal forming the transition metal salt or complex is a transition metal that is able to self-assemble by metallophilic attractions, or the partial oxidation of the thiols to disulfides is carried out.

The self-healing polymer network of the invention can also be defined by its preparation process. Thus, the self-healing material obtainable by the process of the invention is also considered part of the invention.

In a third aspect the invention relates to the self-healing polymer network in the form of a biocompatible hydrogel for use in therapy.

In a fourth aspect, the invention relates to the use of the self-healing polymer network as defined above as a sensor, a filter, an adhesive, a bioadhesive, a thickener, a sealing system, or a medical device, or in the manufacture of self-healing paints, or coatings.

In another aspect the invention relates to an article of manufacture made of the self-healing polymer network of the invention.

In still another aspect the invention relates to a process for the manufacture of an article as defined above, the process comprising forming the article from the self-healing polymer network of the invention.

DETAILED DESCRIPTION OF THE INVENTION

Figure 1:
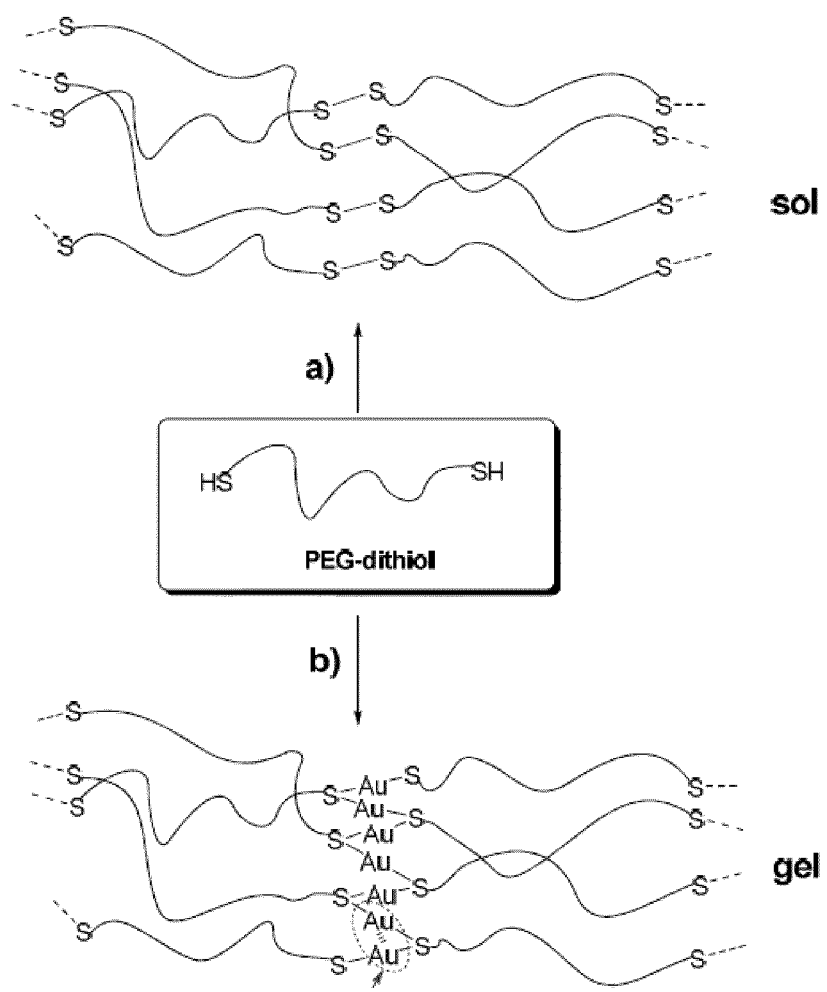
FIG. 1 represents a scheme of the oxidation of a polymer chain functionalized with two thiols promoting chain extension (a) versus Au(I) promoted cross-linking (b). The arrow shows the Au(I)-Au(I) attractive forces responsible of the cross-linking of the polymer chains, so-called aurophilic, or more generally speaking, metallophilic attractions.

The term $M_n$ relates to the number average molecular weight and it is given in Dalton (Da).

The term "M" relates to a transition metal cation.

The term "polymer network" stands for a polymer system crosslinked either by covalent or not-covalent bonds, and relates to the final self-healing product.

The term "polymer chain" stands for a lineal or branched large molecule, or macromolecule, made up of many monomers that are joined together.

The term "metallophilic attractions" relate to M-M attractive forces between neighboring transition metal (M) thiolate centers.

The term "a transition metal able to self-assemble by metallophilic attractions" stands for a transition metal forming part of a thiolate that spontaneously self-assembles by means of attractive forces with other transition metals forming part of other thiolates, when preparing the polymer network of the invention. Examples of such a transition metal (in its oxidation state) able to self-assemble by metallophilic attractions include, but are not limited to Pd(II), Cd(II), Pt(II), Hg(II), Pb(II), Tl(I), Ir(I), Au(I), Ag(I), and Cu(I). Preferably, the transition metal in its oxidation state is Au(I), Ag(I), or Cu(I).

The term "a thiolate other than a transition metal thiolate" stands for any other thiolate that can be oxidized to disulfide. Examples of such thiolates other than a transition metal thiolate include, but are not limited to, alkaline metal thiolates such as lithium, sodium, potassium, rubidium or cesium thiolates, alkaline earth metal thiolates such as beryllium, magnesium, calcium, strontium or barium thiolates, and thiolates of organic cations, such as ammonium, triethylammonium, trialkylammonium, pyridinium, N,N-dimethylaminopyridinium, or protonated 1,8-diazabicyclo[5.4.0]undec-7-ene thiolates, among others. Particularly, the thiolates other than a transition metal thiolate are selected from alkaline metal thiolates such as lithium, sodium, or potassium thiolates, alkaline earth metal thiolates such as calcium thiolate, and thiolates of organic cations, such as the above mentioned.

The term "biocompatible" stands for a substance that is capable of functioning or existing in contact with biological fluid and/or tissue of a living organism with a net beneficial effect on the living organism and which are not otherwise toxic to living systems. In order to obtain a biocompatible self-healing polymer network of the invention both the starting polymer precursors and the transition metals used to the preparation of the polymer network have to be biocompatible. Examples of biocompatible starting polymer precursors giving rise to the biocompatible polymer network of the invention are mentioned below. Examples of transition metal cations giving rise to a biocompatible polymer network according to the invention include, but are not limited to, Au(I), and Ag(I).

As mentioned above, the self-healing polymer network of the invention can be prepared by simply reacting, in the presence of a base, at least one polymer functionalized with at least two thiols with at least one transition metal salt or complex, provided that if the at least one transition metal forming the transition metal thiolate is not a transition metal that is able to self-assemble by metallophilic attractions, then the polymer in a) is functionalized with more that two thiols and the process further comprises the partial oxidation of thiols to disulfides. The process can be carried out at room temperature.

Partial oxidation of thiols to disulfides can be carried out by the addition of a base to the at least one polymer functionalized with at least two thiols, previously to the addition of the at least one transition metal salt or complex. Alternatively, when the salt forming transition metal ion used in the reaction is in an oxidation state higher than one (such as Au(III) or Cu(II)), and it is liable to be reduced by the thiols present in the reaction medium, first a redox reaction between the thiols and the transition metal ion takes place. In such redox reaction, thiols are oxidized to disulfides while the metal is reduced to a lower oxidation state (such as Au(I) or Cu(I)). Then, the transition metal ion reacts with the remaining free thiols to give the corresponding transition metal thiolate needed to provide the self-healing property to the final polymer network. As a way of illustration, ideally the amount of Au(III) added must be not higher than 0.33 equivalents, and the amount of Cu(II) added must not be higher than 0.50 equivalents, with respect to the initial free thiol equivalents.

In a particular embodiment, a partial reduction of thiols to disulfides is carried out so that from 1-99% of the sulfur atoms of the at least one functionalized polymer chain of the obtained polymer network as defined above are in the form of disulfide, and the rest of the sulfur atoms (until completing 100% of sulfur atoms in the form of disulfide, thiol, thiolate, or a mixture thereof) are in the form of a transition metal thiolate, preferably a thiolate of a transition metal that is able to self-assemble by metallophilic attractions, more preferably a Au(I), Ag(I) or Cu(I) thiolate, or a mixture thereof.

The base must be added in order to at least neutralize all the acid derived from the formation of the metal thiolate (generally one mole of acid for each mole of reacting thiol). The base is preferably added in an excess, typically from 2 to 10-fold excess. Preferably, the transition metal salt or complex is a salt or complex of a transition metal that is able to self-assemble by metallophilic attractions, such as a Pd(II), Cd(II), Pt(II), Hg(II), Pb(II), Tl(I), Ir(I), Au(I), Au(III), Ag(I), Cu(I), or Cu(II) salt of complex, more preferably it is selected from a Au(I), Au(III), Ag(I), Cu(I), or Cu(II) salt or complex.

When the polymer functionalized with at least two thiols is a liquid polymer at room temperature, the reaction can be carried out in the absence of a solvent, namely, the at least one transition metal salt or complex in the form of a powder can be added to the liquid polymer.

The reaction can be carried out in the presence of a suitable solvent, such as water or an organic solvent. In such a case, the at least one transition metal salt or complex can be dissolved or dispersed in the solvent and the at least one polymer functionalized with at least two thiols can be added either in the form of a powder or of a solution in a suitable solvent. Alternatively, the salt or complex in the form of a powder can be added to a solution of the functionalized polymer in a suitable solvent.

Suitable organic solvents include, but are not limited to, a ($C_2$-$C_6$)-ether such as diethyl ether ($Et_2O$), or tetrahydrofuran (THF); a ($C_1$-$C_4$) alcohol such as methanol, or ethanol, ethyl acetate, toluene, xylene, hexane, ($C_1$-$C_6$) chlorine containing solvents such as chloroform or dichloromethane, N,N-dimethylformamide (DMF), dimethylsulfoxide (DMSO).

When the process is carried out in an organic solvent an organogel can be obtained. Accordingly, in an embodiment the self-healing polymer network is an organogel. Alternatively, the organic solvent can be removed when the reaction is considered finished in order to obtain the final polymer as an elastomer or a rubber. Accordingly, in an embodiment the self-healing polymer network is an elastomer or a rubber. In another particular embodiment the self-healing polymer network of the invention comprises water in an amount below 1 wt %.

When the process is carried out in water a hydrogel can be obtained. The water content of the hydrogel can be from comprising water in an amount from 1 wt % to 99 wt %. Accordingly, in another embodiment the self-healing polymer is a hydrogel.

When the self-healing polymer of the invention is in form of a hydrogel, the self-healing speed of the hydrogel systems of the invention can be modulated by adjusting the pH. As a way of example, the hydrogel obtained by reaction of PEG-dithiol and a gold salt, is dynamic at slightly basic pH, namely it flows like a Silly Putty® or "slime" and possesses a tremendous and fast self-repairing power. Thus, above pH 7 the gel behaves like a Silly Putty® or "slime". Such slime possesses a powerful self-healing ability, namely it can be cut in two pieces that glue together in less than two minutes. At pH 7, the hydrogel does not flow, but it still presents a very good self-healing ability. As a comparison, at acidic pH, the hydrogel is static (hard, non-flowing and limited self-healing).

The self-healing efficiency depends on the concentration of transition metal thiolate groups (—S-M). The higher the number of thiolate groups, the better the self-healing efficiency of the material. The highest self-healing efficiency is achieved when all the thiols are in form of —S-M groups. It is preferred that the amount of transition metal thiolates in the polymer is equal to or higher than 0.5%, more preferably equal to or higher than 1%, more preferably equal to or higher than 2%, even more preferably equal to or higher than 5%, and most preferably equal to or higher than 10%, with respect to the total amount of sulfur atoms in the form of disulfide bond, thiol, or thiolate group. In a preferred embodiment, M is a transition metal cation that is able to self-assemble by metallophilic attractions, such as Pd(II), Cd(II), Pt(II), Hg(II), Pb(II), Tl(I), Ir(I), Au(I), Ag(I), or Cu(I). More preferably the transition metal cation is Au(I), Ag(I) or Cu(I).

Even in the absence of disulfide crosslinks in the polymer, the dynamic exchange between thiolates of a transition metal that is able to self-assemble by metallophilic attractions, particularly Au(I), Ag(I), Cu(I), together with the spontaneous self-assembly of the resulting transition metal thiolate centers by means of M-M attractive forces (the so-called metallophilic attractions) are the responsible for both the cross-linking (gelation) process and the self-healing ability of the polymer.

Metallophilic cross-linking (FIG. 1b) affords a real three-dimensional network, where multiple macromer terminations are thought to be "sewed" together by a transition metal cation that is able to self-assemble by metallophilic attractions, particularly Au(I), Ag(I) or Cu(I), in a zigzag configuration. Such zigzag self-assembly is particularly strong with Au(I) thiolate complexes, having an improved effect in gelation speed, stability of the system, as well as in the self-healing ability of the resulting polymer network. Accordingly, in a particular embodiment of the first aspect of the invention, the transition metal is Au(I). Additionally, as far as biomedical applications are concerned, the use of Au(I) is advantageous versus the use of gold nanoparticles as the toxicity problems are avoided (the hydrogel system composed of thiolated polyethylene glycol (PEG) chains and gold(I) ions being completely biocompatible) and the amount of gold needed to obtain the self-healing polymer network is reduced. Moreover, the use of Au(I) thiolates in medicine, known as chrysotherapy, is known for more than 50 years (C. F. Shaw et al., "Gold based therapeutic agents", *Chem. Rev.*, 1999, vol. 99, pp. 2589-2600, page 2560 from the article). In another particular embodiment the transition metal ion is Ag(I). Additionally, the use of Ag(I) possesses the advantage of conferring antimicrobial properties to these materials (A. A. Isab, et al, "Synthesis and characterization of thiolate-Ag (I) complexes by solid-state and solution NMR and their antimicrobial activity", *Spectrochimica Acta Part A*, 2007, vol. 66, pp. 364-370, pages 368-369 from the article).

In still another particular embodiment of the self-healing polymer network of the invention, from 1-99% of the sulfur atoms of the at least one functionalized polymer chain are in the form of disulfide, and the rest of the sulfur atoms until completing 100% of said sulfur atoms are in the form of a transition metal thiolate, preferably a thiolate of a transition metal that is able to self-assemble by metallophilic attractions, more preferably a Au(I), Ag(I) or Cu(I) thiolate, or a mixture thereof.

The self-healing polymer network of this particular embodiment can alternatively be prepared by a process which comprises reacting a) at least one disulfide-containing polymer, with b) at least one polymer functionalized with at least two transition metal thiolates, preferably with at least two thiolates of a transition metal that is able to self-assemble by metallophilic attractions, more preferably a with at least two Au(I), Ag(I), or Cu(I) thiolates, in the presence of a base. The process can be carried out at room temperature. Also, the process can be carried out in the presence of a suitable solvent, such as the solvents mentioned herein before. The self-healing polymer network obtainable by this process is also considered part of the invention.

According to this alternative process, sulfurs comprised in at least one of the functionalized polymer chains of the self-healing polymer network of the invention will be forming part of a disulfide, —S—S—, while sulfurs comprised in at least another one of the functionalized polymer chains will be in the form of a transition metal thiolate, preferably of a thiolate of a transition metal that is able to self-assemble by metallophilic attractions, more preferably a thiolate selected from the group Au(I), Ag(I), and Cu(I) thiolate, or mixtures thereof.

Surprisingly, the inventors found that a polymer network cross-linked with disulfide bonds and comprising free thiols showed a self-healing ability at pH>7, but only for a certain period of time, until all the thiols were oxidized to disulfides. Nevertheless, in the absence of free thiols, or when all of them were oxidized to disulfides, the disulfide cross-linked polymer network did not present the mentioned property. Also surprisingly, inventors found that the addition of a small amount of a transition metal salt or complex, preferably of a salt or complex of a transition metal that is able to self-assemble by metallophilic attractions, more preferably of a gold, silver or copper salt or complex, or mixture thereof (being the gold, silver or copper ion in any of their oxidation states) preserved a percentage of thiols against oxidation while keeping their ability to undergo thiolate-disulfide exchange. As a consequence, the polymer kept its self-healing ability.

This fact is illustrated by carrying out the oxidation of a commercially available 4-arm thiol-terminated polyethylene glycol derivative, PEG(SH)$_4$ of $M_n$ 10,000, in the presence of NaOH at room temperature to obtain a disulfide-cross-linked hydrogel (PEG(SS)$_4$), as depicted below

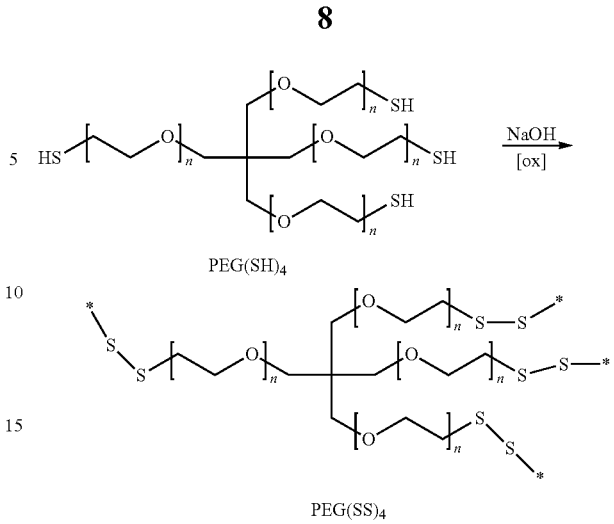

wherein n is such that $M_n$ 10,000. At earlier stages of the oxidation process the material was mechanically quite consistent and showed self-healing ability. This was probably due to that there was still a certain amount of unoxidized thiolate groups. Thus, if such gel was cut in two halves, the fragments were fused together in a question of seconds by simply joining the two pieces together. Without wishing to be bound by theory, this could be attributed to the dynamic character of the thiolate-disulfide exchange, which seems to be very fast at pH>7. It has to be noted that the presence of an amount of free thiolate groups is necessary for this exchange to occur, but at the same time the oxidation of thiols to disulfides is dramatically favored at basic pH. Once the reaction was completed (in about 3-4 days) the obtained hydrogel did not present the mentioned self-healing ability at all.

Figure 2:
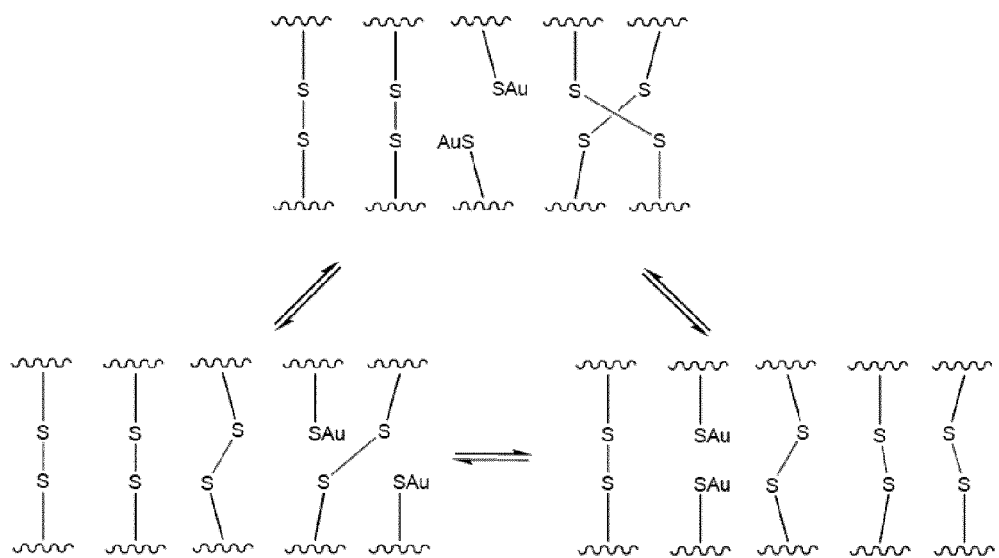
FIG. 2 represents a dynamic network system crosslinked mainly with disulfide bonds. The system represented here would have 80% of the sulfurs connected all the time, in form of disulfide bridges (solid behavior). The remaining 20% of the sulfur atoms would be in form of Au(I) thiolates (healing behavior). As the thiolate-disulfide exchange keeps happening at room temperature and pH>7, all the disulfide bridges will be in constant exchange. This will confer a strong self-healing power to the polymer system.

By the addition of a small amount of a Au(I) thiolate species of formula AuS-PEG-SAu to the PEG(SS)$_4$ system, the polymer recovered its self-healing ability. Therefore, the presence of the Au(I) thiolate, as well as of Ag(I) thiolate or Cu(I) thiolate, seem to guarantee the presence of a certain amount of unoxidized thiolates all the time. At the same time, the majority of the disulfide crosslinks are always connected, what makes the material to be mechanically consistent while keeping the self-healing property (see FIG. 2). The same effect is achieved with other polymer systems comprising disulfide bonds, such as the ones defined herein below.

Oligomeric or polymeric precursors used for the preparation of the polymers functionalized with at least two thiols (thiolated polymers) used in the process of the invention may be of different nature. Examples of such precursors include, but are not limited to:
  synthetic polymers: polyethylene glycol (PEG), acrylates, methacrylates, polyvinyl alcohol (PVA), polypropylene glycol (PPG), polydimethylsiloxane (PDMS), calcium polycarbophil, deacetylated gellan gum;
  natural polymers: polysaccharides such as chitosan, sodium or calcium carboxymethylcellulose, sodium alginate, condroitin sulphate, sodium hydroxypropylcellulose, hyaluronic acid, pectin; peptides, proteins, and oligonucleotides; polyisoprenes, and
  mixtures of the above mentioned synthetic and natural polymers or copolymers made there from.

Accordingly, in one embodiment, the oligomeric or polymeric precursor giving rise to the functionalized polymer chain is selected from the group consisting of calcium polycarbophil (a copolymer of acrylic acid and divinyl glycol), chitosan, sodium carboxymethylcellulose, calcium carboxymethylcellulose, sodium alginate, condroitin sulphate, sodium hydroxypropylcellulose, hyaluronic acid, pectin, poly(acrylic acid), poly(methacrylic acid), polyacrylamide, deacetylated gellan gum, polyethylene glycol, polypropylene glycol (PPG), polydimethylsiloxane (PDMS), polyisoprene, and mixtures thereof.

Particularly, the polymer chain is a linear polyethylene glycol or a multi-arm polyethylene glycol having from 3 to about 10 arms. More particularly, the polymer chain is a multi-arm PEG selected from a 3-arm PEG, 4-arm PEG, a 6-arm PEG, and a 8-arm PEG.

In another embodiment, the oligomeric or polymeric precursor giving rise to the functionalized polymer chain is a non-water-soluble polymer whose $T_g$ (glass transition temperature) is below room temperature, such as PPG, PDMS or polyisoprene, among others. Self-healing polymer networks of the invention derived from these polymers are in the form of a rubber or elastomer.

In another embodiment, the oligomeric or polymeric precursor giving rise to the functionalized polymer chain is selected from a peptide, a protein, an oligonucleotide, and mixtures thereof.

The invention also contemplates a self-healing polymer network wherein the oligomeric or polymeric precursor giving rise to the functionalized polymer chain is a mixture of any of the functionalized polymers mentioned herein above.

The position of the thiols in these polymeric or oligomeric precursors can be terminal (in the extremities) or random, being the number of thiols per polymer or oligomeric chain always equal to or greater than two.

The thiolated polymer can be selected from a thiolated calcium polycarbophil (a copolymer of acrylic acid and divinyl glycol), thiolated chitosan, thiolated sodium carboxymethylcellulose, thiolated calcium carboxymethylcellulose, thiolated sodium alginate, thiolated condroitin sulphate, thiolated sodium hydroxypropylcellulose, thiolated hyaluronic acid, thiolated pectin, thiolated poly(acrylic acid), thiolated poly(methacrylic acid), thiolated polyacrylamide, thiolated deacetylated gellan gum, thiolated polyethylene glycol, thiolated polypropylene glycol, thiolated polydimethylsiloxane, thiolated polyisoprene, and mixtures thereof. From the list above at least the following ones are biocompatible and may be used to obtain self-healing polymers of the invention useful in therapy: a thiolated calcium polycarbophil (a copolymer of acrylic acid and divinyl glycol), thiolated chitosan, thiolated sodium carboxymethylcellulose, thiolated sodium alginate, thiolated sodium hydroxypropylcellulose, thiolated hyaluronic acid, thiolated pectin, thiolated poly(acrylic acid), thiolated poly(methacrylic acid), thiolated polyacrylamide, and thiolated polyethylene glycol. More particularly, the thiolated polymer is a thiolated polyethylene glycol, and even more particularly PEG-dithiol, 3-arm PEG-trithiol, 4-arm PEG-tetrathiol, 6-arm PEG hexathiol or 8-arm PEG-octathiol, all of them commercially available. The thiolated polymer can also be thiolated PPG, thiolated PDMS or thiolated polyisoprene. The last one may be prepared as described in S. Bokern et al., "Synthesis of New Thermoplastic Elastomers by Silver Nanoparticles as Cross-Linker", *Macromolecules,* 2011, vol. 44, pp 5036-5042).

Thiolated polymers obtained from a peptide, a protein, an oligonucleotide, and mixtures thereof, can also be used in the process of the invention.

Additionally, derivatives of the above-mentioned polymers may also be used in the process of the invention. Examples of such derivatives comprise derivatives obtained by auto-cross-linking, introduction of functional groups, attachment of complexing agents (such as, e.g., EDTA), coupling of enzyme inhibitors, and so on.

The thiolated polymers used in the preparation of the self-healing polymer network of the invention are either commercially available or can be prepared by thiolation of the above mentioned polymers by conventional methods. For economical reasons, the use of cysteine groups lends itself for thiolation because the thiolated polymer is easy and inexpensive to obtain. Cysteine groups may preferably be bound to the polymer via an amide bond. As a way of illustration, the thiolated polymer can also be prepared by using Traut's reagent, addition of thioacetic acid to double bonds, nucleophilic substitution of haloalkanes with potassium thioacetate, and other known conventional methods. Particular examples of processes to obtain thiolated polymers that can be used in the process of the invention can be found, for example, in U.S. Pat. No. 7,354,600 and A. Bernkop-Schnürch et al. "Thiomers: A new generation of mucoadhesive polymers", *Advanced Drug Delivery Reviews,* 2005, vol. 57, pp. 1569-1582.

On the other hand, the polymer according to the invention may also be prepared in such a way that, in the course of producing said polymer, at least one monomer having thiols is (co)-polymerized, which monomer comprises free thiols in the polymer, i.e. the thiol is not directly reacted in the polymerization reaction. Alternatively one co-monomer can have functional groups that are easily converted into thiols after polymerization, using conventional techniques described above.

Examples of transition metal salts used in the process of the invention include, but are not limited to, $HAuCl_4$, AuCl, $AgNO_3$, AgTFA, $CuCl_2$, CuCl, and CuO. Particularly, the metal transition metal salt is selected from $HAuCl_4$, $AgNO_3$, AgTFA and $CuCl_2$. More particularly the metal transition metal salt is $HAuCl_4$, $AgNO_3$ and AgTFA.

Examples of transition metal complex used in the process of the invention include, but are not limited to, [AuCl(PPh$_3$)$_2$], and [AuBr(PPh$_3$)$_2$] (for the synthesis of gold(I) complexes, see for example: M. C. Gimeno et al., "Three- and Four-Coordinate Gold(I) Complexes", *Chemical Reviews,* 1997, vol. 97, pp. 511-522).

Thiolated polymers mentioned above can also be used to prepare the starting disulfide-containing polymer used in the process of the invention comprising mixing a) at least one disulfide-containing polymer, and b) at least one polymer functionalized with at least two transition metal thiolates. Thus, disulfide-containing polymers can be obtained by oxidation, for instance by the addition of a base, of any one of the thiolated polymers mentioned above, or mixtures thereof. Alternatively, the oxidation of thiols to disulfides can be carried out using other reagents, such as halogens (bromine or iodine) or a mixture of $H_2O_2/I_2$.

Other disulfide-containing polymers obtained by different processes can also be used. As an instance, the disulfide-containing polymers can be polymers obtained by the oxidation of the thiolated polymers disclosed above. Particularly, the disulfide-containing polymers are polymers obtained by the oxidation of a thiolated polyethylene glycol, such as PEG-dithiol, 3-arm PEG-trithiol, 4-arm PEG-tetrathiol, 6-arm PEG hexathiol or 8-arm PEG-octathiol, and more particularly, by the oxidation of PEG-dithiol or 4-armed PEG-tetrathiol, namely the disulfide-containing polymer is PEG(SS)$_2$ or PEG(SS)$_4$.

The polymer functionalized with at least two Au(I), Ag(I), or Cu(I) thiolate groups used in one of the processes of the invention can be obtained from the polymer functionalized with at least two thiols mentioned above, by reaction with an aqueous solution of an Au(I), Ag(I) or Cu(I) salt, more preferably of an Au(I) salt. Preferably, the polymer functionalized with at least two transition metal thiolated groups is M-S-PEG-S-M, wherein M is Au, Ag or Cu, more preferably Au—S-PEG-S—Au. Also preferably, the polymer functionalized with at least two transition metal thiolated groups is M-S—PPG-S-M, wherein M is Au, Ag or Cu, more preferably Ag—S—PPG-S—Ag.

The molecular weight of the thiolated polymer, the disulfide-containing polymer, and the polymer functionalized with at least two transition metal thiolates, preferably with at least two thiolates of a transition metal that is able to self-assemble by metallophilic attractions, more preferably a with at least two Au(I), Ag(I), or Cu(I) thiolates is not critical. In an embodiment, their molecular weight is from 1,000 to 100,000 Da. Particularly, their molecular weight is from 2,000 to 20,000, and more particularly from 3,400 to 10,000. Preferably, when the disulfide-containing polymers is PEG-dithiol, the molecular weight is 3,400, and when the disulfide-containing polymers is PEG-tetrathiol the molecular weight is 10,000.

As mentioned above, the processes of the invention are carried out in the presence of a base. Examples of bases, include, but are not limited to, sodium hydroxide (NaOH), sodium bicarbonate (NaHCO$_3$), sodium carbonate (Na$_2$CO$_3$), triethylamine (NEt$_3$), pyridine, N,N-dimethylaminopyridine (DMAP), and 1,8-diazabicyclo[5.4.0]undec-7-ene (DBU).

The processes of the invention, whether in the absence or in the presence of disulfide bonds, can be carried out at room temperature. By room temperature it is understood a temperature comprised between 15 and 30° C. Thus, unlike most of the prior art processes, the processes of the present invention can be carried out without the need of heating or applying any other external stimulus, which is advantageous since they are easy to carry out at industrial scale.

The self-healing material of the invention can be degraded by several different methods or mechanisms, depending if there are disulfide bridges in the polymer network or just metallophilic cross-linking. This can be very useful for the recyclability of such self-healing materials, particularly in the case of elastomers. The addition of an excess of any monofunctional thiol can result in the degradation of the network in all cases, due to thiolate-disulfide or thiolate-thiolate exchange. The addition of dithiothreitol (DTT), sodium borohydride, phosphines or similar reducing agents can also result in the degradation of disulfide-containing networks of the invention. Finally, the addition of metal coordinating compounds, such as tris(2-carboxyethyl)phosphine (TCEP) or triphenylphosphine can also result in the degradation of the polymer network of the invention, due to its ability to coordinate metal ions.

As mentioned above, the self-healing polymer network of the invention can be in the form or a hydrogel. Accordingly, in an embodiment, the self-healing hydrogel polymer of the invention is a biocompatible hydrogel that can have application in different areas such as biomedicine (A. S. Hoffman, "Hydrogels for biomedical applications" *Advanced Drug Delivery Reviews*, 2002, vol. 54, pp. 3-12, abstract from page 3), drug delivery (T. R. Hoare, et al., "Hydrogels in drug delivery: Progress and challenges", *Polymer*, 2008, vol. 49, pp. 1993-2007, abstract from page 1993), cell culture and scaffolds for tissue engineering (J. L. Drury, et al., "Hydrogels for tissue engineering: scaffold design variables and applications", *Biomaterials*, 2003, vol. 24, pp. 4337-4351, abstract from page 4337). Therefore, these uses also form part of the invention. Accordingly, the invention also relates to the self-healing material in form of a biocompatible hydrogel as defined above for use in therapy. The process of the invention provides the possibility of obtaining the hydrogel in vivo by injecting the components separately into the body area of interest, in such a way that they self-assemble to form the structure sought. So, the invention also relates to a kit for the in situ preparation of a self-healing polymer network in form of an hydrogel as defined above, the kit comprising a) at least one polymer functionalized with at least two thiols, with b) at least one transition metal salt or complex; or a) at least one disulfide-containing polymer, with b) at least one polymer functionalized with at least two transition metal thiolate groups; together with instructions for the preparation in situ of the polymer network. As it will be apparent to those skilled in the art, when the self-healing hydrogel polymer network of the invention is to be used in therapy it must be biocompatible.

As a way of illustration, the kit can comprise the following two solutions: a solution A (of at least one transition metal salt or complex selected from the group consisting of Au(I), Au(III), Ag(I), Cu(I) or Cu(II) salt or complex) and a solution B (at least one polymer functionalized with at least two thiols, such as PEG dithiol or tetrathiol), and optionally a special syringe system. For the in situ formation of the hydrogel, the content of solution A is charged in one syringe and the content of solution B in another syringe. Then, the 2 solutions are injected very slowly, for instance, with the aid of a syringe system comprising two syringes that end up in the same needle. Alternatively the 2 solutions can be injected in the same point added via two conventional syringes. The hydrogel is formed nearly instantaneously.

In a particular embodiment, the self-healing polymer network of the invention can be useful for the antiarthritic treatment, chrysotherapy (C. F. Shaw, "Gold-based therapeutic agents", *Chemical Reviews*, 1999, vol. 99, pp. 2589-2600, text from page 2590), as a viscosupplementation agent for osteoarthritis (C. J. Bell, et al., "Self-assembling peptides as injectable lubricants for osteoarthritis", *Journal of Biomedical Materials Research Part A*, 2006, vol. 78A, pp. 236-246, abstract from page 236), as a muco-adhesive agent (A. Bernkop-Schnurch, "Thiomers: A new generation of mucoadhesive polymers", *Advanced Drug Delivery Reviews*, 2005, vol 57, pp. 1569-1582, abstract from page 1569), and as an antimicrobial agent (A. A. Isab, et al, "Synthesis and characterization of thiolate-Ag(I) complexes by solid-state and solution NMR and their antimicrobial activity", *Spectrochimica Acta Part A*, 2007, vol. 66, pp. 364-370, pages 368-369 from the article).

Accordingly, in an embodiment the invention relates to a hydrogel self-healing polymer network as defined above for use in the treatment of a disease or condition selected from the group consisting of arthritis, osteoarthritis, a bacterial infection, and a cold. In an embodiment, the transition metal cation (M) is Ag(I) and the disease is a bacterial infection. In another embodiment, M is Au(I) and the disease is rheumatoid arthritis. In another particular embodiment, M is Au(I) and the disease is osteoarthritis.

So, the invention is related to the use of the self-healing hydrogel of the invention for the manufacture of a medicament for the treatment of a disease or condition selected from arthritis, osteoarthritis, a bacterial infection, and a cold, the hydrogel being biocompatible.

This aspect of the invention can also be formulated as a method of treating a disease or condition as defined above in an animal, including a human, comprising administering to the animal an effective amount of a the self-healing polymer network as defined above in combination with one or more pharmaceutically acceptable excipients or carriers.

In another embodiment, the self-healing polymer network of the invention can be useful as a sensor (Y. J. Song et al., "A self-repairing polymer waveguide sensor", *Smart Materials and Structures*, 2011, 20, article number: 065005, page 1, abstract), an adhesive (H. Jin, et al., "Fracture and fatigue response of a self-healing epoxy adhesive", *Polymer*, 2011, 52, pp. 1628-1638, first page of the article, page 1628), a bioadhesive, or a thickener, a sealing system, among others. Therefore, these uses also form part of the invention.

In another embodiment, the self-healing polymer network of the invention can be useful in the manufacture of self-healing paints and coatings (S. H. Cho et. al., "Self-Healing Polymer Coatings", *Advanced Materials*, 2009, 21, pp. 645-649, first page of the article, page 645).

Furthermore, the present invention covers all possible combinations of particular and preferred groups described hereinabove.

In still another embodiment, the self-healing polymer network of the invention is in the form of an elastomer or a rubber. According to this embodiment, the self-healing polymer network of the invention can be useful in widespread everyday applications, such as sealants (M. Y. L. Chew, "Curing characteristics and elastic recovery of sealants", *Building and Environment*, 2001, vol. 36, pp. 925-929, first page of the article, page 925), expansion joints (T. Yun, et al., "A performance evaluation method of preformed joint sealant: Slip-down failure", *Construction and Building Materials*, 2011, vol. 25, pp. 1677-1684, first page of the article, page. 1677), structural adhesives (R. Keshavaraj et al., "Effects of moisture on structural silicone rubber sealants used in window glazing applications", *Construction and Building Materials*, 1994, vol. 8, pp. 227-232, first page of the article, page. 227), and silicon molds (S. Chung, et al., "Evaluation of micro-replication technology using silicone rubber molds and its applications", *International Journal of Machine Tools and Manufacture*, 2003, vol. 43, pp. 1337-1345, pages 1337 and 1338 of the article).

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Comparative Example 1

In order to obtain a disulfide-cross-linked hydrogel system, in an Eppendorf tube, a 4-armed PEG-tetrathiol of $M_n$ 10,000 (50 mg; Sigma-Aldrich) was dissolved in water (980 µL) and 1N NaOH (20 µL) was added. The reaction was monitored by performing the Ellman's test (as disclosed in G. Bulaj et al. Biochemistry, 1998, vol. 37, pp. 8965-8972) until the disappearance of all the —SH groups was complete. The mixture was allowed to stand at room temperature for 96 hours. After this time, a transparent hydrogel was obtained, resulting from cross-linking promoted by the oxidation of thiols to disulfide. The resulting hydrogel, $PEG(SS)_4$, showed the typical characteristics of a thermoset.

In order to test its self-healing ability, the obtained hydrogel was broken in small pieces, introduced into an Eppendorf tube and allowed to stand for 24 hours. No self-healing was observed.

The following Examples 1-6 relate to the preparation of hydrogels according to the present invention. Hydrogels are made from a thiolated polymer and a transition metal salt.

Example 1

Self-Healing Hydrogel from 4-Arm PEG Tetrathiol and Au(III)

Figure 5:
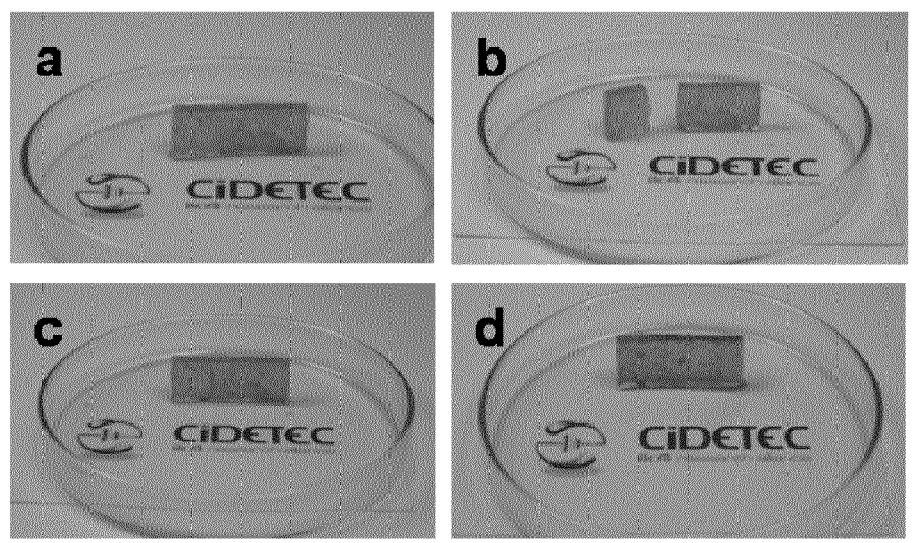
FIG. 5 represents the self-healing process in 1 minute of the hydrogel obtained according to Example 1.

To a solution of 4-arm PEG-tetrathiol of $M_n$ 10,000 (60 mg) in water (590 µL), an aqueous solution of 2 mM phenol red (10 µL) was added as a pH indicator. On the other hand, to an aqueous solution of Au (III) (4.88 mmol $HAuCl_4$ 1M), water (570 µL) and a solution of 5M NaOH (20 µL) were added. The two solutions were combined and the mixture was allowed to stand for 24 hours, obtaining a consistent hydrogel. Then, the resulting hydrogel was removed and kept for 15 hours in a mold. The resulting hydrogel was cut in half, and subsequently the 2 halves were joined and allowed to stand for 1 minute. After this period, the hydrogel was completely restored and in one piece (FIG. 5). The process could be repeated several times without observing any decrease in the self-healing power.

Example 2

Self-Healing Hydrogel from 4-Arm PEG-Tetrathiol and Ag(I)

To a solution of 4-arm PEG-tetrathiol of Mn 10,000 (25 mg) in water (0.5 mL), a 1N $AgNO_3$ solution (10 µL) was added. In less than one minute a transparent hydrogel was formed. Finally, an aqueous solution of NaOH was added until pH>7, to obtain a self-healing hydrogel.

Example 3

Self-Healing Hydrogel from 4-Arm PEG-Tetrathiol and Au(I)

A 1N Au(I) solution (10 µL; prepared according to the procedure described for the synthesis of gold sodium N-acetylcysteine dihydrate in D. T. Hill et. al., "Gold-197 Mossbauer Studies of Some Gold (I) Thiolates and Their Phosphine Complexes Including Certain Antiarthritic Gold Drugs", Inorganic Chemistry, 1983, 22, p. 2937) was added to a solution of 4-arm PEG-tetrathiol of $M_n$ 10,000 (25 mg) in water (0.5 mL). In less than one minute a transparent hydrogel was formed. Finally, an aqueous solution of NaOH was added until pH>7, to obtain a self-healing hydrogel.

Example 4-6

Similarly as in examples 2 and 3 above, hydrogels of Examples 4-6 were obtained from:
PEG-dithiol ($M_n$ 3,400) by the addition of an Ag(I) solution;
a mixture of PEG-dithiol ($M_n$ 3,400) and 4-armed PEG-tetrathiol ($M_n$ 10,000) by addition of either a Ag(I) solution; and
a mixture of PEG-dithiol ($M_n$ 3,400) and 4-armed PEG-tetrathiol ($M_n$ 10,000) by addition of either a Ag(I) or a Au(I) solution.
In all cases a transparent hydrogel was formed.

Example 7 and Comparative Example

Figure 3:
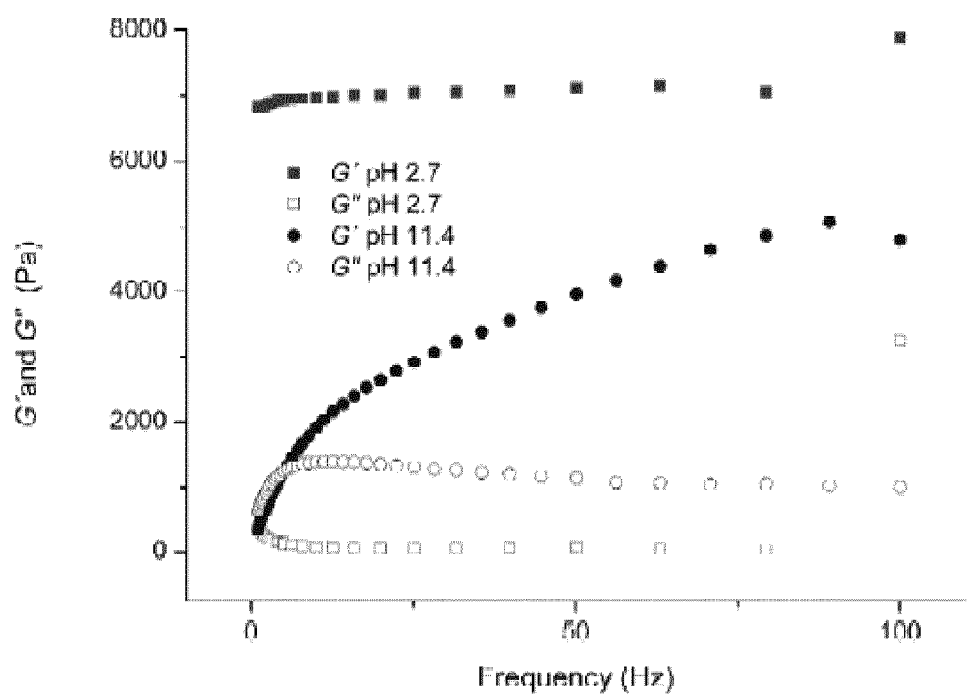
FIG. 3. Storage (G', filled symbols) and loss (G", empty symbols) moduli as a function of frequency for a 5 wt % hydrogel with 0.8 equivalents of Au(I) (relative to thiol equivalents) at pH 2.7 ("steady" hydrogel) and at pH 11.4 ("living" hydrogel).

Rheological Behaviour of Two Hydrogels of the Same Composition Depending on the pH A hydrogel was obtained by adding a solution of Au(I) (0.8 equivalents; prepared as in Example 3) to an aqueous PEG-dithiol solution (5 wt %) at pH 11.4. As shown by FIG. 3, at basic pH the hydrogel was in the form of a "slime" exhibiting different rheology depending on the frequency. At low frequencies the material had a liquid like behavior, but when the frequency reached 5 Hz G' increased above G", emblematic of gel behavior.

By way of comparison, another hydrogel was obtained following the same process as above but at pH 2.7. As also shown by FIG. 3, at acidic pH the hydrogel showed a behavior typical for covalently cross-linked hydrogels, with G' values about two orders of magnitude higher than G".

Example 8

Self-Healing Hydrogel from PEG-Dithiol and Au(I)

To a solution of PEG-dithiol (30 mg; Sigma Aldrich, $M_n$ 3,400) in water (472 µL) a 2 mM aqueous solution of phenol red (5 µL) was added. Then a 0.1M aqueous solution of Au (I) (12.32 µmol; prepared as in Example 3) was added. This solution was basified with 5N NaOH (20 µL). The mixture was stirred and allowed to stand for 5 minutes. The resulting viscous solution was used as such for the experiments described below.

To check its self-healing power, the resulting hydrogel was cut in half, and subsequently the 2 halves were joined and allowed to stand for 15 seconds. After this period, the hydrogel was completely restored and in one piece. The process could be repeated several times without observing any decrease in the self-healing power. After one month the self-healing power of the hydrogel remained intact.

Examples 9-11 below relate to the preparation of self-healing hydrogels made from a disulfide-containing polymer and a gold(I) thiolate.

Example 9

Figure 4:
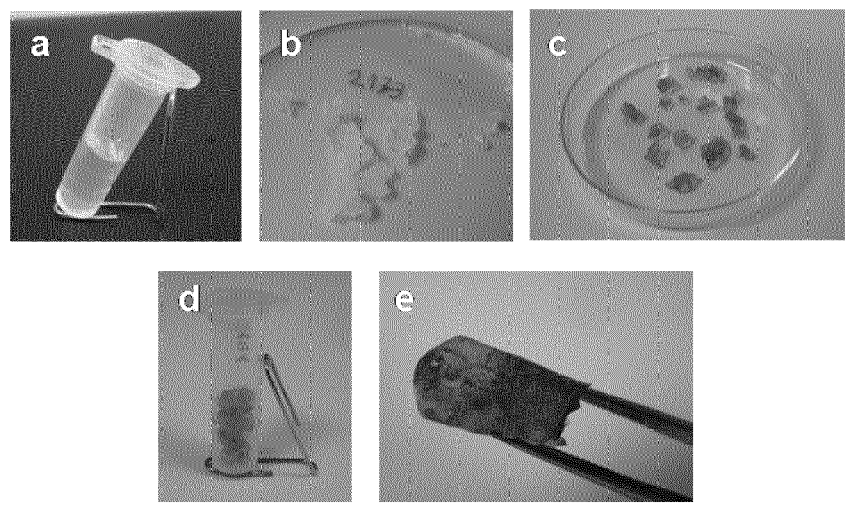
FIG. 4 shows photographs of disulfide-crosslinked polyethylene glycol, $PEG(SS)_4$, before (a) and after (b) breaking it into small pieces. Then the $PEG(SS)_4$ fragments were mixed with a small amount of a gold(I) thiolate (c). Then the resulting fragments were allowed to stand in an Eppendorf tube at room temperature for 24 h (d). After this period, the hydrogel was completely restored into one single piece (e).

The hydrogel obtained in the Comparative Example 1 was broken in small pieces, and the gold(I) thiolate solution obtained in Example 8 (100 µL) was added and mixed with a spatula. Then, all the fragments were introduced into the Eppendorf tube and allowed to stand for 24 hours. After this period, a completely restored hydrogel was obtained (FIG. 4b-d). The breaking-healing process was repeated several times without observing any decrease in the self-healing power of the polymer.

Example 10

Figure 6:
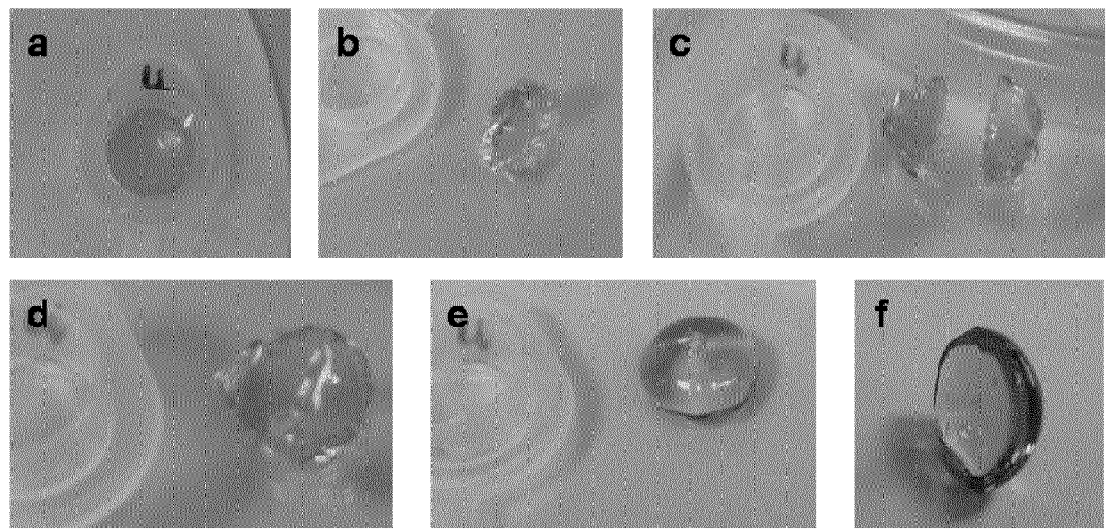
FIG. 6 represents the self-healing process of the hydrogel obtained according to Example 10.

In an Eppendorf tube, 4-arm PEG-tetrathiol of $M_n$ 10,000 (50 mg) was dissolved in water (970 µL), and 1N NaOH (20 µL) and an aqueous solution of 2 mM phenol red (10 µL) were added. Then, 100 µL of the mixture were put in an Eppendorf cap and let to stand at room temperature for 48 hours. Afterwards, the gold(I) thiolate solution obtained in Example 8 (0.5 µL) was added and the mixture was allowed to stand for 24 hours (FIG. 6a). Then, the resulting hydrogel (FIG. 6b) was cut in half with a scalpel (FIG. 6c). The two halves were put together and allowed to stand for 24 hours (FIG. 6d). After this period, the hydrogel was completely restored and in one piece (FIG. 6e, f). The process could be repeated several times without observing any decrease in the self-healing power.

Example 11

Self-Healing Hydrogel from 4-Arm PEG-Tetrathiol and Au (III)

To a solution of 4-arm PEG-tetrathiol (30 mg; Sigma-Aldrich, $M_n$ 10,000) in water (560 µL), 5M NaOH (40 µL) was added, and the resulting solution was left open to air for 96 hours. After this time, an oxidized hydrogel was obtained. Then, a solution of 4-arm PEG (90 mg) and water (872 µL), an aqueous solution of 2 mM phenol red (10 µL), aqueous 1M $HAuCl_4$ (7.68 µmol) and 5N NaOH (20 µL) were added. The mixture was stirred and allowed to stand for 24 hours. The resulting gel was introduced into a rectangular shape mold. The resulting hydrogel was cut in half, and then the two halves were put together and allowed to stand for 5 minutes. After this period, the hydrogel was completely restored in one single piece.

Example 12

Self-Healing Polyurethane Elastomer

Synthesis of Thiol-Functionalized PPG

Thiol functionalized poly(propylene glycol) was synthesized in a 250 mL glass reactor equipped with mechanical stirrer and a vacuum inlet. A silicon oil bath was employed to heat the reaction system to the desired temperature. A two step reaction method was required to obtain the desired thiol functionalized poly(propylene glycol). In the first step, poly (propylene glycol) (PPG) (50 g, $M_n$ 8,000) and isophorone diisocyanate (IPDI) (2.78 g) were fed into the flask reactor in a 1:2 molar relation. The reaction was catalyzed with 50 ppm of dibutyl tin diacetate (DBTDA) and proceeded at 70° C. for 2 h under vacuum and with mechanical stirring. In the second step, the reactor was cooled down to room temperature and then a solution of cysteamine (0.96 g) in THF was added in the same molar relation as IPDI. The reaction proceeded for 20 minutes and the resulting thiol-functionalized PPG, designate as $PPG(SH)_2$, was stored in a tightly closed glass bottle.

Synthesis of Self-Healing Polyurethane Elastomer

Figure 7:
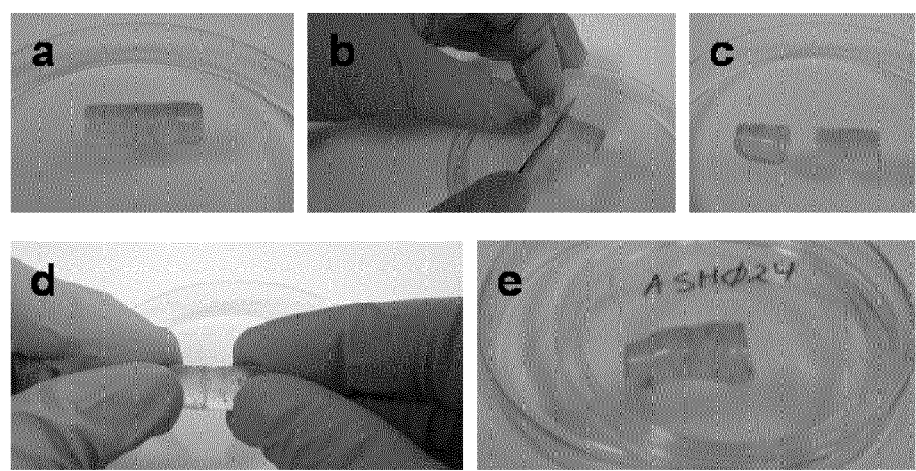
FIG. 7 represents the self-healing process of the PPG elastomer obtained according to Example 12. The cylindrical-shaped elastomer (a) was cut in 2 pieces (b,c). Then the 2 pieces were put together (d) and allowed to stand in contact for 6 hours. After this time the material was completely restored into one single piece (e).

In a 10 mL vial, $PPG(SH)_2$ (1.45 g), Mesamoll® (plasticizer based on alkylsulfonic phenyl ester) (0.55 g) and triethylamine (100 mg) were added and mixed with magnetic stirring. Then, a solution of silver trifluoroacetate in xylene 1N (344 µL) was added dropwise. A transparent yellowish and mechanically consistent gel was obtained which was placed on to a cylindrical open mold for 16 h. To test the self-healing ability of the material, the resulting specimen was cut with a sharp cutter and after a few seconds the two pieces were put in contact again. Six hours later the specimen was completely restored into one single piece (see FIG. 7).

Example 13

Synthesis of Self-Healing Silicone Elastomer

In a 10 mL vial, thiol-terminated silicone fluid (1 g, GP-974, from Genesse Polymers Corporation) and triethylamine (27 mg) were added and mixed with magnetic stirring. Then, a 1N solution of silver trifluoroacetate in THF (89 µL)

was added drop-wise. A transparent orange-yellowish and mechanically consistent gel was obtained, which was then placed on to a cylindrical open mold for 16 h. After this period of time the solvent had completely evaporated, to give a silicone elastomer. The elastomer was then cut in two pieces, and then the two halves were put together and allowed to stand for 1 hour. After this period, the elastomer was completely restored in one single piece.

Example 14

Kit Comprising 4-Arm PEG Tetrathiol and Au(III) Solutions

A kit comprised a solution A which is 4-arm PEG-tetrathiol ($M_n$ 10,000, 60 mg) in phosphate buffer pH 7.4 (600 μL), and a solution B which is aqueous 1M $HAuCl_4$ (4.88 μL) and aqueous 1N NaOH (20 μL) in phosphate buffer pH 7.8 (575 μL). The content of solution A is charged in one syringe and the content of solution B in another syringe. Then, in order to form in situ a self-healing polymer network in form of a hydrogel, the 2 solutions are injected very slowly in the same point via two conventional syringes. When injected in the body area of interest, a hydrogel is formed in about 30 seconds.

Example 15

Biocompatibility

The assay was carried out to determine the biocompatibility of a self-healing hydrogel obtained as in the Example 1, and a control hydrogel, obtained as in Comparative Example 1. Both, self-healing hydrogel and the control hydrogel were purified by dialysis during 1 week before the assay (Snake-Skin Dialysis Tubing from ThermoScientific 3,500 MWCO) and lyophilized. Both samples were sterilized in autoclave. A stable cell-line of Hela was employed in the assay. Cell viability was measured by a MTS test and the proliferation was measured by cell counting for three days.

Figure 8:
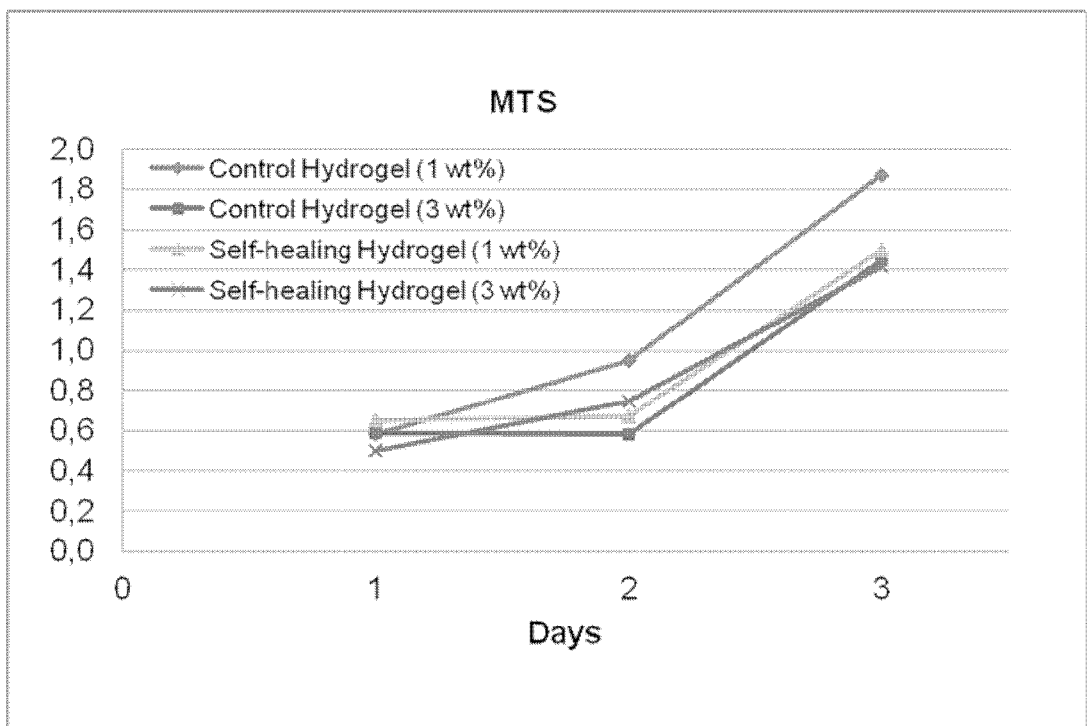
FIG. 8 represents the values obtained in an in vitro MTS colorimetric assay for the hydrogel obtained on Comparative Example 1 (control) and for the self-healing hydrogel obtained in Example 1 during the day 1, 2 and 3 of the assay.
Figure 9:
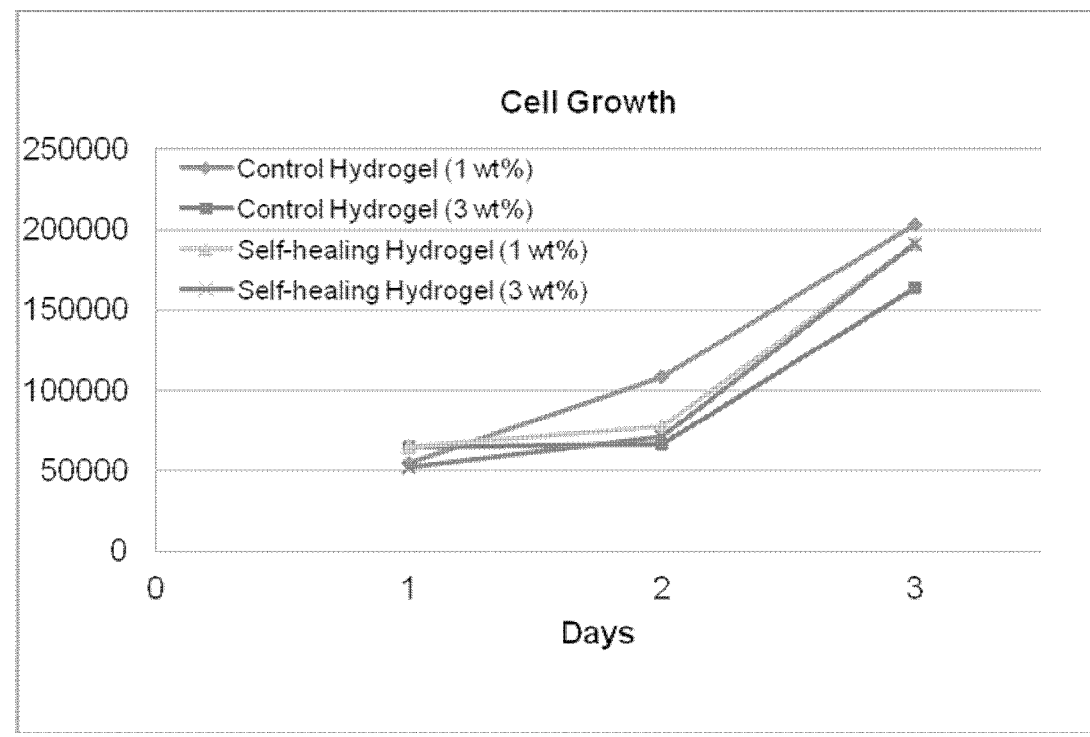
FIG. 9 represents the average alive cell number values obtained in a cell counting assay for the hydrogel obtained on Comparative Example 1 (control) and for the self-healing hydrogel obtained in Example 1 during the day 1, 2 and 3 of the assay.

Cell culture was carried out in a non-treated 24-well multiwell plate, and the hydrogel was placed in a polyethylene terephthalate (PET) insert of 0.4 micron pore size (Millipore). Both samples were tested in 1 wt % and 3 wt % concentrations. Lyophilized samples were reconstituted with Hela culture media and were kept swollen during 5 days before seeding to ensure the stability of the gels on the culture media. Hela culture media was added during those days to ensure adequate hydration of the gels. After 5 days cells were seeded in a concentration of 26,000 cells/well and a volume of 0.8 mL, and incubated at 37° C. Cell viability and proliferation tests were destructive, and enough wells were seeded for all the experiments for three days. The mechanical properties of the gels were constant during the assay. In days 1, 2 and 3 of the assay, the insert and culture media were removed. Cells were washed with phosphate-buffered saline (×1), and detached with trypsin/EDTA 0.25 mg/mL (4 minutes and 37° C.). Cells were re-suspended in 0.5 mL of Hela media. This cell suspension was employed for the MTS assay (3×100 microliter) and for cell counting (200 microliter). Results obtained from the MTS assays (shown in FIG. 8) show that both self-healing hydrogel and control hydrogel allow cell viability. Cell counting assay is shown in FIG. 9, where normal cell growth is observed after 3 days.

Example 16

Self-Healing Polyacrylamide with Au (I)

10 μL of an aqueous solution of phenol red (2.0 mM) was added, as a pH indicator, to an aqueous solution of poly [(acrylamide)$_{0.94}$-co-(2-mercaptoethyl acrylamide)$_{0.60}$] ($M_w$=46,400 g/mol, PDI 1.26, [SH]=0.356 μmol/mg) containing 50 mg in 490 μL of deionised water. Separately, 5.93 μL of an aqueous solution of $HAuCl_4$ at 1.0M was diluted with 474 μL of deionised water. This solution was added to the polyacrylamide solution to give a yellow hydrogel. Finally a solution of 5.0M NaOH (20 μL) was added to obtain a self-healing hydrogel after a quick stirring. Self-healing hydrogels were also obtained with other example of poly [(acrylamide)$_x$-co-(2-mercaptoethyl acrylamide)$_{1-x}$] (with 0.90<x<0.98 and 6,500 g/mol<$M_w$<200,000 g/mol) and the quantity of thiol could be varied: 0.200 μmol/mg<[SH] <0.800 μmol/mg. For high molecular weight polymers (Mw>100,000 g/mol), self-healing properties were observed 1 day after adding the aqueous solution of NaOH.

Example 17

Self-Healing Polyacrylamide with Ag (I)

10 μL of an aqueous solution of phenol red (2.0 mM) was added, as a pH indicator, to an aqueous solution containing 50 mg of poly[(acrylamide)$_{0.94}$-co-(2-mercaptoethyl acrylamide)$_{0.06}$] ($M_w$=46,400 g/mol, PDI 1.26, [SH]=0.356 μmol/mg) in 490 μL of deionised water. Separately, 17.8 μL of an aqueous solution of $AgNO_3$ (Ag (I), 1.0M) was diluted with 474 μL of deionised water. This solution was added to the polyacrylamide solution and the mixture gave a yellow hydrogel. Finally a solution of 5M NaOH (20 μL) was added and a self-healing hydrogel was obtained after a quick stirring. Self-healing hydrogels were also obtained with other example of poly[(acrylamide)$_x$-co-(2-mercaptoethyl acrylamide)$_{1-x}$] (with 0.90<x<0.98 and 6,500 g/mol<$M_w$<200,000 g/mol) and the quantity of thiol could be varied: 0.200 μmol/mg<[SH]<0.800 μmol/mg. For high molecular weight polymers (Mw>100,000 g/mol), self-healing properties were observed 1 day after adding the aqueous solution of NaOH.

Example 18

Self-Healing Gelatin B Hydrogel Au as an Example of Mixed Polypeptides and Proteins 50 mg of thiolated gelatin B (40,000 g/mol, [SH]=0.126 μmol/mg) were dissolved in 490 μL of deionised water. 10 μL of a 2 mM phenol red solution was added to the gelatin solution as pH indicator. 2.1 μL of an aqueous solution of $HAuCl_4$ at 1.0M solution was diluted in 483 μL of diluted water. The diluted gold solution was added dropwise to the gelatin solution and a yellow hydrogel was formed. Finally 15 μL of an aqueous solution of NaOH at 5.0M was added to the gel. The gel was left to settle for 1 day and a pink-colored self-healing hydrogel was obtained.

Example 19

Self-Healing Hyaluronic Acid Hydrogel Au as an Example of glycosaminoglycan 50 mg of commercial thiolated hyaluronic acid (Gelin-S® from Glycosan, [SH]=0.182 μmol/mg) were dissolved in 490

μL of deionised water. 10 μL of a 2.0 mM phenol red solution was added to the gelatin solution as pH indicator. 2.4 μL of an aqueous solution of HAuCl$_4$ at 1.0M solution was diluted in 485 μL of diluted water. The diluted gold solution was added dropwise to the gelatin solution and a yellow hydrogel was formed. Finally 2 μL of an aqueous solution of NaOH at 5.0M was added to the gel. The gel was left to settle for 1 day and a pink-colored self-healing hydrogel was obtained.

Example 20

Self-Healing Polyurethane I

In a 10 mL flask, thiol-functionalized PPG [PPG(SH)$_2$] (1.45 g), Mesamoll® (plasticizer based on alkylsulfonic phenyl ester) (0.55 g) and triethylamine (100 mg) were added and mixed with magnetic stirring. Then, a solution of silver trifluoroacetate in xylene 1N (344 μL) was added drop-wise. Suddenly a transparent yellowish and mechanically consistent gel was obtained, which was placed on to a cylindrical open mold for 16 h, to yield the desired elastomeric polyurethane. To test the self-healing ability of the material, the resulting specimen was cut with a sharp cutter and after a few seconds the two pieces were put in contact again. Six hours later the specimen was completely restored into one single piece (see FIG. 7).

Example 21

Self-Healing Polyurethane II

In a banbury type internal mixer, thiol-functionalized PPG [PPG(SH)$_2$] (45 g), triethylamine (400 mg) and a solution of silver trifluoroacetate (880 mg) in THF (1 mL) were added and mixed at 30 r.p.m for 10 minutes. A transparent yellowish and mechanically consistent rubber was obtained which was placed on to a rectangular mold under pressure for 5 minutes. To test the mechanical and self-healing properties of the material tensile test specimens were made. The resulting specimens were cut with a sharp cutter and after a few seconds the two pieces were put in contact again. Six hours later the specimen was completely restored into one single piece.

REFERENCES CITED IN THE APPLICATION

1. WO2010128007A1
2. WO2010087912
3. Y-S. Chen, et al. "Assessment of the In Vivo Toxicity of Gold Nanoparticles", Nanoscale Res. Lett., 2009, vol. 4, pp. 858-864.
4. C. F. Shaw et al., "Gold based therapeutic agents", Chem. Rev., 1999, vol. 99, pp. 2589-2600.
5. A. A. Isab, et al, "Synthesis and characterization of thiolate-Ag(I) complexes by solid-state and solution NMR and their antimicrobial activity", Spectrochimica Acta Part A, 2007, vol. 66, pp. 364-370.
6. S. Bokern et al., "Synthesis of New Thermoplastic Elastomers by Silver Nanoparticles as Cross-Linker", Macromolecules, 2011, vol. 44, pp 5036-5042.
7. U.S. Pat. No. 7,354,600
8. A. Bernkop-Schnurch et al. "Thiomers: A new generation of mucoadhesive polymers", Advanced Drug Delivery Reviews, 2005, vol. 57, pp. 1569-1582.
9. M. C. Gimeno et al., "Three- and Four-Coordinate Gold(I) Complexes", Chemical Reviews, 1997, vol. 97, pp. 511-522.
10. A. S. Hoffman, "Hydrogels for biomedical applications" Advanced Drug Delivery Reviews, 2002, vol. 54, pp. 3-12.
11. T. R. Hoare, et al., "Hydrogels in drug delivery: Progress and challenges", Polymer, 2008, vol. 49, pp. 1993-2007.
12. J. L. Drury, et al., "Hydrogels for tissue engineering: scaffold design variables and applications", Biomaterials, 2003, vol. 24, p. 4337-4351.
13. C. J. Bell, et al., "Self-assembling peptides as injectable lubricants for osteoarthritis", Journal of Biomedical Materials Research Part A, 2006, vol. 78A, pp. 236-246.
14. Y. J. Song et al., "A self-repairing polymer waveguide sensor", Smart Materials and Structures, 2011, 20, article number: 065005
15. H. Jin, et al., "Fracture and fatigue response of a self-healing epoxy adhesive", Polymer, 2011, 52, pp. 1628-1638.
16. S. H. Cho et. al., "Self-Healing Polymer Coatings", Advanced Materials, 2009, 21, pp. 645-649.
17. M. Y. L. Chew, "Curing characteristics and elastic recovery of sealants", Building and Environment, 2001, vol. 36, pp. 925-929.
18. T. Yun, et al., "A performance evaluation method of preformed joint sealant: Slip-down failure", Construction and Building Materials, 2011, vol. 25, pp. 1677-1684.
19. R. Keshavaraj et al., "Effects of moisture on structural silicone rubber sealants used in window glazing applications", Construction and Building Materials, 1994, vol. 8, pp. 227-232.
20. S. Chung, et al., "Evaluation of micro-replication technology using silicone rubber molds and its applications", International Journal of Machine Tools and Manufacture, 2003, vol. 43, pp. 1337-1345.
21. G. Bulaj et al. "Ionization-Reactivity Relationships for Cysteine Thiols in Polypeptides", Biochemistry, 1998, vol. 37, pp. 8965-8972.
22. D. T. Hill et al., "Gold-197 Moessbauer studies of some gold(I) thiolates and their phosphine complexes including certain antiarthritic gold drugs", Inorganic Chemistry, 1983, vol. 22, pp. 2936-2942.

The invention claimed is:

1. A self-healing polymer network comprising at least one polymer chain functionalized with at least two sulfur atoms in the form of thiol, thiolate or forming part of a disulfide, or a mixture thereof, wherein from 0.1-100% of the sulfur atoms are in the form of at least one transition metal thiolate S-M, wherein M is a transition metal cation, and from 99.9-0% of said sulfur atoms are in the form of thiol, a thiolate other than a transition metal thiolate, or forming part of a disulfide until completing 100% of the sulfur atoms in the form of disulfide, thiol, or thiolate, provided that if there are not cross-links in form of disulfide, then the at least one transition metal forming the transition metal thiolate is a transition metal that is able to self-assemble by metallophilic attractions.

2. The self-healing polymer network according to claim 1, wherein the amount of transition metal thiolates in the polymer is equal to or higher than 0.5%, with respect to the total amount of sulfur atoms in the form of disulfide, thiol, or thiolate.

3. The self-healing polymer network according to claim 1, wherein the at least one transition metal forming the transition metal thiolate is a transition metal that is able to self-assemble by metallophilic attractions.

4. The self-healing polymer network according to claim 1, wherein the polymer chain is selected from the group consisting of calcium polycarbophil (a copolymer of acrylic acid and divinyl glycol), chitosan, sodium carboxymethylcellulose, calcium carboxymethylcellulose, sodium alginate, condroitin sulphate, sodium hydroxypropylcellulose, hyaluronic acid, pectin, poly(acrylic acid), poly(methacrylic acid), poly(acrylamide), deacetylated gellan gum, polyethylene glycol, polypropylene glycol (PPG), polydimethylsiloxane (PDMS), polyisoprene, a peptide, a protein, an oligonucleotide, and a mixture thereof.

5. The self-healing polymer network according to claim 4, wherein the polymer chain is a linear or multi-arm polyethylene glycol having from 3 to about 10 arms.

6. The self-healing polymer network according to claim 1, wherein the transition metal thiolate is selected from the group consisting of Au(I), Ag(I), and Cu(I) thiolate.

7. The self-healing polymer network according to claim 6, wherein the transition metal thiolate is Au(I) or Ag(I) thiolate.

8. The self-healing polymer network according to claim 1, wherein from 1-99% of the sulfur atoms are in the form of disulfide, and the rest of the sulfur atoms until completing 100% of said sulfur atoms are in the form of a thiolate.

9. The self-healing polymer network according to claim 1, which is a hydrogel, an elastomer, or a rubber.

10. A process for the preparation of the self-healing polymer network of claim 1, comprising reacting:
a) at least one polymer functionalized with at least two thiols, with
b) at least one transition metal salt or complex,
in the presence of a base,
wherein:
if the polymer in a) is functionalized with only two thiols, then the transition metal forming the transition metal salt or complex is a transition metal that is able to self-assemble by metallophilic attractions; or
if the polymer in a) is functionalized with more than two thiols then either the transition metal forming the transition metal salt or complex is a transition metal that is able to self-assemble by metallophilic attractions, or the partial oxidation of the thiols to disulfide is carried out.

11. A process for the preparation of the self-healing polymer network of claim 8, the process comprising reacting:
a) at least one disulfide-containing polymer, with
b) at least one polymer functionalized with at least two transition metal thiolates S-M,
wherein M is a transition metal cation,
in the presence of a base.

12. An article of manufacture made of the self-healing polymer network according to claim 1.

13. The article of manufacture of claim 12, which is a medical device.

14. A method for detection which comprises providing the self-healing polymer network as defined in claim 9 as a sensor.

15. A method for filtering which comprises providing the self-healing polymer network as defined in claim 9 as a filter.

16. A method for adhering which comprises providing the self-healing polymer network as defined in claim 9 as an adhesive.

17. A method for sealing which comprises providing the self-healing polymer network as defined in claim 9 as a sealing system.

18. A method for the manufacture of a self-healing paint which comprises providing the self-healing polymer network as defined in claim 9 as an additive for a paint.

19. A method for coating a substrate which comprises applying to the substrate the self-healing polymer network as defined in claim 9 as a coating.

20. The self-healing polymer network according to claim 1, wherein the transition metal thiolate is selected from the group consisting of Pd(II), Cd(II), Pt(II), Hg(II), Pb(II), Tl(I), Ir(I), Au(I), Ag(I) and Cu(I) thiolate.

* * * * *